US010544451B2

(12) United States Patent
Jiang et al.

(10) Patent No.: US 10,544,451 B2
(45) Date of Patent: Jan. 28, 2020

(54) VESICULAR LINKER AND USES THEREOF IN NUCLEIC ACID LIBRARY CONSTRUCTION AND SEQUENCING

(71) Applicant: MGI Tech Co., Ltd., Shenzhen (CN)

(72) Inventors: Yuan Jiang, Shenzhen (CN); Jing Guo, Shenzhen (CN); Xiaojun Ji, Shenzhen (CN); Chunyu Geng, Shenzhen (CN); Kai Tian, Shenzhen (CN); Xia Zhao, Shenzhen (CN); Huaiqian Xu, Shenzhen (CN); Wenwei Zhang, Shenzhen (CN); Hui Jiang, Shenzhen (CN); Radoje Drmanac, Los Altos Hill, CA (US)

(73) Assignee: MGI TECH CO., LTD., Shenzhen (CN)

( * ) Notice: Subject to any disclaimer, the term of this patent is extended or adjusted under 35 U.S.C. 154(b) by 305 days.

(21) Appl. No.: 15/510,890

(22) PCT Filed: Nov. 21, 2014

(86) PCT No.: PCT/CN2014/091852
§ 371 (c)(1),
(2) Date: Mar. 13, 2017

(87) PCT Pub. No.: WO2016/037416
PCT Pub. Date: Mar. 17, 2016

(65) Prior Publication Data
US 2017/0356039 A1     Dec. 14, 2017

Related U.S. Application Data

(63) Continuation-in-part of application No. PCT/CN2014/086418, filed on Sep. 12, 2014.

(51) Int. Cl.
| | | |
|---|---|---|
| *C12Q 1/6853* | (2018.01) |
| *C12N 15/66* | (2006.01) |
| *C12Q 1/6806* | (2018.01) |
| *C40B 40/08* | (2006.01) |
| *C40B 50/06* | (2006.01) |
| *B01J 19/00* | (2006.01) |
| *C12N 15/10* | (2006.01) |
| *C12Q 1/6811* | (2018.01) |
| *C12Q 1/6837* | (2018.01) |
| *C12Q 1/686* | (2018.01) |
| *C40B 60/14* | (2006.01) |
| *C12Q 1/6855* | (2018.01) |
| *C12Q 1/6874* | (2018.01) |
| *C12N 9/22* | (2006.01) |
| *C12N 9/00* | (2006.01) |
| *C12N 11/06* | (2006.01) |
| *C40B 50/14* | (2006.01) |

(52) U.S. Cl.
CPC ........ *C12Q 1/6853* (2013.01); *B01J 19/0046* (2013.01); *C12N 9/22* (2013.01); *C12N 9/93* (2013.01); *C12N 11/06* (2013.01); *C12N 15/10* (2013.01); *C12N 15/1065* (2013.01); *C12N 15/1082* (2013.01); *C12N 15/1093* (2013.01); *C12N 15/66* (2013.01); *C12Q 1/6806* (2013.01); *C12Q 1/686* (2013.01); *C12Q 1/6811* (2013.01); *C12Q 1/6837* (2013.01); *C12Q 1/6855* (2013.01); *C12Q 1/6874* (2013.01); *C40B 40/08* (2013.01); *C40B 50/06* (2013.01); *C40B 50/14* (2013.01); *C40B 60/14* (2013.01); *B01J 2219/00529* (2013.01); *C12Q 2565/537* (2013.01)

(58) Field of Classification Search
CPC .................................................. C12Q 1/6853
USPC ............................................................. 506/9
See application file for complete search history.

(56) References Cited

U.S. PATENT DOCUMENTS

| | | |
|---|---|---|
| 2007/0172839 A1 | 7/2007 | Smith et al. |
| 2010/0069263 A1 | 3/2010 | Shendure et al. |
| 2012/0122161 A1 | 5/2012 | Musgrave-Brown et al. |

FOREIGN PATENT DOCUMENTS

| | | |
|---|---|---|
| CN | 102181943 A | 9/2011 |
| CN | 102296065 A | 12/2011 |
| CN | 103014137 A | 4/2013 |
| CN | 103103624 A | 5/2013 |
| WO | 01/40516 A2 | 6/2001 |
| WO | 2007076420 A2 | 7/2007 |
| WO | 2007/087291 A2 | 8/2007 |
| WO | 2007087291 A2 | 8/2007 |
| WO | 2007140417 A2 | 12/2007 |
| WO | 2008070352 A2 | 6/2008 |
| WO | 2008070375 A2 | 6/2008 |
| WO | 2009/061840 A1 | 5/2009 |
| WO | 2009/133466 A2 | 11/2009 |
| WO | 2012037876 A1 | 3/2012 |
| WO | 2012037880 A1 | 3/2012 |
| WO | 2012079486 A1 | 6/2012 |

(Continued)

OTHER PUBLICATIONS

International Search Report issued for PCT/CN2014/091852, dated Jun. 9, 2015.

(Continued)

*Primary Examiner* — Karla A Dines
(74) *Attorney, Agent, or Firm* — Westman, Champlin & Koehler, P.A.; Z. Peter Sawicki; Amanda M. Prose

(57) ABSTRACT

Provided are a vesicular linker and a single-chain cyclic library constructed by using the linker. The library can be used for RNA sequencing and other sequencing platforms dependent on a single-stranded cyclic library, and has the advantages of high throughput sequencing, high accuracy and simple operations.

17 Claims, 2 Drawing Sheets

Specification includes a Sequence Listing.

(56) References Cited

FOREIGN PATENT DOCUMENTS

| WO | 2012162267 A2 | 11/2012 |
| WO | 2016/078095 A1 | 5/2016 |
| WO | 2016/078096 A1 | 5/2016 |

OTHER PUBLICATIONS

Written Opinion of the International Searching Authority issued for PCT/CN2014/091852, dated Jun. 9, 2015.
Ukai H., et al. "A new technique to prevent self-ligation of DNA" Journal of Biotechnology vol. 97, Dec. 31, 2002, pp. 233-242.
International Search Report issued for PCT/CN2014/086418, dated Jun. 15, 2015.
Written Opinion of the International Searching Authority issued for PCT/CN2014/086418, dated Jun. 15, 2015.
Office Action dated Nov. 13, 2018 for CN application 201480081687.4.
English Translation of Office Action dated Nov. 13, 2018 for CN application 201480081687.4.
Smith D R, "Ligation-mediated PCR of restriction fragments from large DNA molecules" PCR Methods & Applications, Cold Spring Harbor Laboratory Press, Genome Res. 1992 2: 21-27.
Bennett E A et al, "Library construction for ancient genomics: single strand or double strand?", Biotechniques Rapid Dispatches, Informa Healthcare, US, vol. 56, No. 6, Jun. 1, 2014, pp. 289-290.
Gansauge, Marie-Theres et al, "Single-stranded DNA library preparation for the sequencing of ancient or damaged DNA", Nature Protocols, vol. 8, No. 4, Mar. 14, 2013, pp. 737-748.
Gansauge, Marie-Theres et al, "Single-stranded DNA library preparation from highly degraded DNA using T4 DNA ligase", Nucleic Acids Research, vol. 45, No. 10, Jan. 23, 2017.
Extended European Search Report issued for related application No. EP14901593.5, dated Jun. 13, 2017.
Office action from JPO for JP application 2017513705, dated Apr. 23, 2018.

SEQUENCE LISTING

```
<160> NUMBER OF SEQ ID NOS: 5

<210> SEQ ID NO 1
<211> LENGTH: 41
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<223> OTHER INFORMATION: n is a, t, c or g
<220> FEATURE:
<221> NAME/KEY: misc_feature
<222> LOCATION: (12)..(12)
<223> OTHER INFORMATION: n is a, c, g, or t

<400> SEQUENCE: 1
gtcctaagac cngatcgggc ttcgactgga gactccgact t                         41

<210> SEQ ID NO 2
<211> LENGTH: 28
<212> TYPE: DNA
<213> ORGANISM: Artificial Sequence
<220> FEATURE:
<223> OTHER INFORMATION: Oligonucleotide

<400> SEQUENCE: 2
agtcggaggc caagcggtct taggacat                                        28
```

```
<210> SEQ ID NO 3
<211> LENGTH: 41
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (11)..(20)
<223> OTHER INFORMATION: Tag sequence
<220> FEATURE:
<221> NAME/KEY: misc_feature
<222> LOCATION: (11)..(20)
<223> OTHER INFORMATION: n is a, t, c or g

<400> SEQUENCE: 3
agacaagctc nnnnnnnnnn gatcgggctt cgactggaga c                41

<210> SEQ ID NO 4
<211> LENGTH: 25
<212> TYPE: DNA
<213> ORGANISM: Artificial Sequence
<220> FEATURE:
<223> OTHER INFORMATION: Oligonucleotide

<400> SEQUENCE: 4
tcctaagacc gcttggcctc cgact                                  25

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide

<400> SEQUENCE: 5
tcgagcttgt cttcctaaga ccgc                                   24
```

VESICULAR LINKER AND USES THEREOF IN NUCLEIC ACID LIBRARY CONSTRUCTION AND SEQUENCING

CROSS-REFERENCE TO RELATED APPLICATION

This application is the U.S. national phase of PCT Application No. PCT/CN2014/091852 filed on Nov. 21, 2014, which claims a priority to and benefits of PCT Application No. PCT/CN2014/086418, filed with the State Intellectual Property Office of P. R. China on Sep. 12, 2014, the entire contents of which are incorporated herein by reference.

FIELD

The present disclosure relates to the field of biotechnology, in particular, to a vesicular adaptor and a method for constructing a nucleic acid library and a method for sequencing the same.

BACKGROUND

The second-generation sequencing technology, also known as Next-generation sequencing technology, is named corresponding to the first-generation sequencing technology which is represented by Sanger sequencing method. The second-generation sequencing technology is represented by Roche/454 Pyrosequencing, Illumina/Solexa polymerase synthesis sequencing and ABI/SOLiD ligase sequencing, and their common characteristics are high sequencing throughput. Compared with these mainstream sequencing platforms, Complete Genomics (CG) sequencing platform with the highest throughput may produce 9.9 TB of data in each run, and its output may reach 50 Gb per hour, which is 10-25 times that of the mainstream of the sequencing platform. With respect to read length for haploidy, among the mainstream sequencing platforms, only the Illumina sequencer may achieve a read length of 8-10 kb to haploidy, while the CG sequencer may reach a read length greater than 99 kb. In addition, the CG sequencer may achieve accuracy up to 99.999%, better than other commercial sequencers. Thus, compared with the mainstream sequencing platforms, CG sequencing platform has its unique advantages.

In the process of constructing a nucleic acid sequencing library, it is generally necessary to introduce an adaptor with a known sequence for sequencing. However, it has been reported that the adaptor is ligated for library construction in such an existing way that not only ligating efficiency is not high enough, but also many by-products at low come along. In addition, as CG sequencing platform adopts a cyclic single-stranded library for sequencing, thus linear double-stranded libraries constructed by the mainstream sequencing platforms are not suitable for the CG sequencers. However, as to the method for constructing the cyclic single-stranded library for the nucleic acid sequencing, there is no literature has been reported so far.

Based on above situations, an adaptor with high ligating efficiency and accuracy is urgently required to be developed in the related art.

SUMMARY

An object of the present disclosure is to provide in embodiments a vesicular adaptor for constructing a cyclic single-stranded library for the nucleic acid sequencing in highly efficiency.

Another object of the present disclosure is to provide in embodiments a method for constructing the cyclic single-stranded library and a method for sequencing the same.

In embodiments of a first aspect of the present disclosure, an oligonucleotide vesicular adaptor for constructing a nucleic acid library is provided, the oligonucleotide vesicular adaptor includes:

a 5' paired double-stranded region at a first terminal of the adaptor, including a phosphorylated terminal base;

a 3' paired double-stranded region at a second terminal of the adaptor, including a sticky terminal; and a vesicular non-paired region between the 5' paired double-stranded region and the 3' paired double-stranded region, wherein the vesicular non-paired region includes a first strand and a second strand non-complementary with each other and the first strand is of a length longer than that of the second strand.

In an embodiment of the present disclosure, the sticky terminal of the 3' paired double-stranded region has a tailed single base.

In an embodiment of the present disclosure, the tailed single base is thymine (T).

In an embodiment of the present disclosure, a portion or whole of the first strand of the vesicular non-paired region is used as a region for paring with a sequencing primer.

In an embodiment of the present disclosure, the region for paring with the sequencing primer includes:

optionally a first part, being at least a portion of a first strand of the 5' paired double-stranded region and located upstream of the first strand of the vesicular non-paired region;

a second part, being a portion or whole of the first strand of the vesicular non-paired region;

and optionally a third part, being at least a portion of a first strand of the 3' paired double-stranded region and located downstream of the first strand of the vesicular non-paired region.

In an embodiment of the present disclosure, the vesicular adaptor is of a length of at least 20 nt, preferably 25 to 50 nt, and more preferably 30 to 45 nt.

In an embodiment of the present disclosure, the first strand of the vesicular non-paired region is longer than the second strand of the vesicular non-paired region by at least 5 to 30 nt.

In an embodiment of the present disclosure, the 5' paired double-stranded region has a blunt terminal or a sticky terminal.

In an embodiment of the present disclosure, the sticky terminal of the 5' paired double-stranded region has 1 to 3 non-complementary bases.

In an embodiment of the present disclosure, the vesicular adaptor includes a sense strand and an antisense strand, and is of a structure of formula I from the 5' terminal to the 3' terminal:

$$Y_0\text{-}Y_1\text{-}Y_2 \qquad (I)$$

in which $Y_0$ represents the 5' paired double-stranded region, and is of a length of 10 to 15 nt, preferably 11 nt;

$Y_1$ represents a non-paired double-stranded region, whose sense strand is of a length 5 to 30 nt longer than that of the antisense strand;

$Y_2$ represents the 3' paired double-stranded region.

In an embodiment of the present disclosure, the vesicular adaptor has the following sequences:

```
                                                        (SEQ ID NO.: 1)
5'-GTCCTAAGACCNGATCGGGCTTCGACTGGAGACTCCGACTT-3'

(SEQ ID NO.: 2)
5'-/phos/AGTCGGAGGCCAAGCGGTCTTAGGACAT-3'
```

In embodiments of a second aspect of the present disclosure, a kit is provided. The kit includes:

a container;

an oligonucleotide vesicular adaptor for constructing a library provided in embodiments of the first aspect of present disclosure, wherein the oligonucleotide vesicular adaptor is contained in the container;

a first primer, specifically paring with the first strand of the vesicular non-paired region;

a second primer, specifically paring with the second strand of the vesicular non-paired region; and an instruction.

In an embodiment of the present disclosure, the first primer is used as a sequencing primer.

In an embodiment of the present disclosure, the adaptor is contained in a container.

In embodiments of a third aspect of the present disclosure, a method for constructing a cyclic single-stranded library is provided. The method includes:

(a) end-repairing a double-stranded DNA fragment to obtain a double-stranded DNA fragment with blunt terminals;

(b) adding an adenine (A) base to the 3'-terminal of the double-stranded DNA fragment with the blunt terminals obtained in (a), to obtain a double-stranded DNA fragment with the A base at the 3'-terminal thereof;

(c) ligating an oligonucleotide vesicular adaptor to each terminal of the double-stranded DNA fragment with the A base at the 3'-terminal thereof obtained in (b) to obtain a double-stranded DNA fragment ligated with the oligonucleotide vesicular adaptor at each terminal thereof;

(d) subjecting the double-stranded DNA fragment ligated with the oligonucleotide vesicular adaptor at each terminal thereof obtained in (c), as a template, to a PCR amplification with a pair of primers specifically targeting a sequence of the oligonucleotide vesicular adaptor so as to obtain a DNA amplified product, wherein one of the pair of primers is marked with biotin;

(e) isolating single-stranded DNAs from the DNA amplified product obtained in (d) using beads coated with avidins through "avidin-biotin" combination;

(f) subjecting the single-stranded DNAs obtained in (e) to cyclization in the presence of cyclic single-stranded molecules, so as to obtain the cyclic single-stranded library, a mixture containing a cyclic product.

In an embodiment of the present disclosure, the double-stranded DNA fragment ligated with the oligonucleotide vesicular adaptor at each terminal thereof obtained in (c) has a structure of formula III:

K1-K2-K3                                            (III)

in which,

K1 represents one vesicular adaptor described above;

K2 represents an arbitrary DNA sequence (sequence of a fragment to be sequenced);

K3 represents another vesicular adaptor described above, in which K1 and K3 are connected to K2 respectively at two terminals of K2.

In an embodiment of the present disclosure, K2 is of a length of about 150 bp to about 250 bp.

In an embodiment of the present disclosure, the method further includes:

(g) digesting uncyclized single-stranded DNAs contained in the mixture obtained in (f) with nucleases specifically digesting linear DNAs to obtain a pre-product; and (h) purifying the pre-product obtained in (g) to obtain the cyclic single-stranded library.

In an embodiment of the present disclosure, the double-stranded DNA fragment in (a) is prepared by:

(a0) fragmenting an mRNA sample to obtain fragmented mRNAs; and (a1) reverse transcribing the fragmented mRNAs to obtain cDNA amplified product as the double-stranded DNA fragments.

In an embodiment of the present disclosure, the double-stranded DNA fragment in (a) is obtained by fragmenting a DNA sample.

In an embodiment of the present disclosure, the avidin in (e) is streptavidin.

In an embodiment of the present disclosure, the pair of primers in (d) includes:

a forward primer:

```
                                                        (SEQ ID NO.: 3)
5-/phos/AGACAAGCTCNNNNNNNNNNNGATCGGGCTTCGACTGGAGAC;
and A reverse primer:
                                                        (SEQ ID NO.: 4)
5-/bio/TCCTAAGACCGCTTGGCCTCCGACT,
``` in which,

5-/phos/ indicates that the 5' terminal nucleotide is modified by phosphorylation;

NNNNNNNNNN represents a tag sequence, where N represents adenine (A), thymine (T), cytosine (C) or guanine (G); and 5-/bio/ indicates that the 5' terminal nucleotide is marked with biotin.

In an embodiment of the present disclosure, the cyclic single-stranded molecule in (f) is of a sequence: TCGAGCTTGTCTTCCTAAGACCGC (SEQ ID NO.: 5).

In an embodiment of the present disclosure, the nucleases used in (g) are exonucleases.

In an embodiment of the present disclosure, the nucleases used in (g) include first exonucleases specifically digesting linear single-stranded DNAs and second exonucleases specifically digesting linear double-stranded DNAs.

In an embodiment of the present disclosure, the nucleases include an enzyme mixture of Exo I and Exo III.

In embodiments of a fourth aspect of the present disclosure, a sequencing library is provided. The sequencing library is constructed by the method according to embodiments of the third aspect of the present disclosure.

In embodiments of a fifth aspect of the present disclosure, use of the sequencing library according to embodiments of the fourth aspect of the present disclosure as a library for high throughput sequencing platform is provided.

In an embodiment of the present disclosure, the high throughput sequencing platform is such a sequencing platform that requires a cyclic single-stranded library.

In an embodiment of the present disclosure, the high throughput sequencing platform is Complete Genomics sequencing platform.

It should be appreciated that, within the scope of the present disclosure, the individual technical feature described hereinbefore and hereinafter (e.g., in examples) may be combined with each other to form a new or preferred technical solution, which will not be elaborated herein.

DETAILED DESCRIPTION

Figure 1:
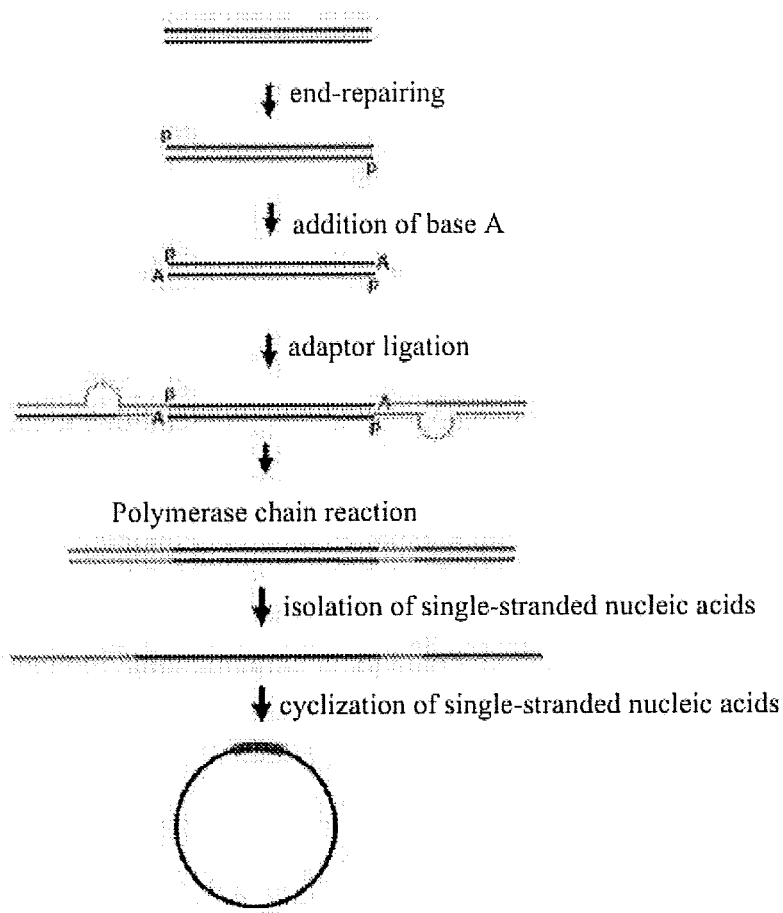
FIG. 1 is a flow chart showing the method for constructing a nucleic acid library according to an embodiment of the present disclosure.

The present inventors have for the first time developed a vesicular adaptor for efficiently constructing a nucleic acid sequencing library with high quality through extensive and in-depth studies and extensive screening. The experimental results show that, compared with sequencing data obtained from other nucleic acid sequencing library construction techniques, the nucleic acid sequencing library constructed with the vesicular adapter of the present disclosure has a higher quality and correlation, which can be used in CG sequencing platform, thereby obtaining high authentic and reliable data without adverse influence on information analysis. Based on this, the present invention has been completed.

CG Sequencing Platform

For CG sequencing platform, DNA nanoballs are embedded in a chip using high-density DNA nanochip technology, and bases in the sequence are read with combinatorial probe anchor ligation (cPAL) technology.

Cyclic single-stranded DNAs were obtained after library construction. A DNA nanoball (DNB), including more than 200 copies of cyclic single-stranded DNAs, was formed by rolling circle amplification, and then embedded into a hole in a chip using high-density DNA nanochip technology, with each hole can only accommodate one DNA nanoball (as one DNA nanoball, once combined with the hole in the chip, will exclude the combination of other DNA nanoballs with the same hole). The occupancy rate of the DNA nanochip was over 90%, and each prepared DNA nanochip may accommodate 180 billion bases for imaging.

The cPAL technique uses probes marked with four different colors to read bases adjacent to the adaptor by at most 10 consecutive bases for each time. As each sequencing is independent from one another, i.e. the sequencing result is not affected by a previous sequencing result, thus avoiding error accumulation, which resulting in high accurate sequencing result with a base error rate as low as $1/100000$. During sequencing, an anchor molecule is added to complementary pair with the adaptor, then the probes marked with four different colors are paired with corresponding bases of the template with the DNA ligases. The types of bases are determined by imaging fluorescent groups. Another advantage of cPAL technology is that, concentrations of probes and enzymes may be greatly reduced as the bases are read using a non-continuous and non-linkage combinatorial probe anchor ligation (cPAL) technology. Different from Sequencing by Synthesis, several bases may be read once in each cycle of cPAL, such that consumptions of sequencing reagents and imaging time may be both greatly reduced. Compared with the current popular next-generation sequencing technology, methods for constructing a library and sequencing the same according to embodiments of the present disclosure may obtain much more data under the premise of consuming fewer reagents.

Method for Constructing a Library

A RNA sample was digested with DNase I. The digested RNAs were purified with RNA clean magnetic beads. mRNAs from the total RNAs were isolated and purified with Oligo (dT) 25 magnetic beads, followed by fragmented to obtain fragmented mRNAs. cDNAs were synthesized by reverse transcription of the fragmented mRNAs, and then end-repaired to form DNA fragments with blunt terminals, which were added with A bases to obtain DNA fragments each with one A base at the 3'-terminal thereof. The obtained DNA fragments each with one A base at the 3'-terminal thereof were ligated with vesicular adaptors to obtain DNA fragments each ligated with the vesicular adaptor at each terminal thereof, which were purified with magnetic beads and then amplified through polymerase chain reaction (PCR) where one primer used is marked with biotin PCR product thus obtained was isolated by magnetic beads coated with streptavidin to obtain PCR single-stranded product, which was cyclized by bridge oligonucleotides and T4 ligases. Uncyclized PCR single-stranded product was enzymatically digested to obtain the cyclic single-stranded library.

Cyclic Single-Stranded Library

The present disclosure also provides in embodiments a cyclic single-stranded library, which is suitable for sequencing and constructed by above-described method for constructing a library of the present disclosure.

In a preferred embodiment of the present disclosure, the present inventors have fully verified the stability, repeatability, and true reliability of the method of the present disclosure by exploring the optimum condition for constructing the library and comparing the results obtained under the optimum condition with that obtained by the other techniques. In addition, it is proved through several experiments to different samples that, the sequencing data obtained by the cyclic single-stranded library of the present disclosure is truly credible.

The advantages of the present disclosure lie in that:

(1) The vesicular adaptor for constructing nucleic acid library is invented for the first time.

(2) With the use of vesicular adaptor in embodiments of the present disclosure in the construction of the nucleic acid library, both the ligating efficiency and the efficiency of subsequent PCR are high and follow-up steps are few.

(3) The nucleic acid library in embodiments of the present disclosure may also be used in a sequencing platform which needs a cyclic single-stranded library.

(4) The method provided in embodiments the present disclosure is of high sequencing throughput, high accuracy and simple operations.

(5) The method provided in embodiments the present disclosure is of high stability, repeatability and reliability.

The present disclosure will be further described in the following with reference to specific embodiments. It should be appreciated that, these embodiments are merely used to illustrate the present disclosure and shall not be construed to limit the scope of the present disclosure. Experimental methods in the following embodiments, not specified the detail conditions, will be carried out according to conventional conditions, such as what is described in Sambrook et al., Molecular Cloning: Laboratory Manual (New York:

Cold Spring Harbor Laboratory Press, 1989), or in accordance with conditions proposed by the manufacturer. Percentages and parts are by weight, unless otherwise stated.

Material and Method

In the following embodiments, the reagent was prepared as follows: 5× first strand buffer contain: 80-400 mM sodium chloride, 10-80 mM magnesium chloride, 200 mM to 300 mM Tris-HCl, phosphate, and water as solvent, with pH of 8.0-8.5. The standard substance, universal human reference RNA, was purchased from Agilent, such RNA is a mixture of 10 kinds of human cell lines (breast cells, hepatoma carcinoma cells, cervical cells, embryonic cells, malignant glioma cells, melanoma cells, liposarcoma cells, lymphoma cells, leukemia T cells, and bone marrow B lymphocyte).

DNA fragments were purified by Ampure XP magnetic beads.

The materials used in embodiments of the present disclosure all are commercially available, unless specified otherwise.

Embodiment 1

Construction of RNA library with the use of the vesicular nucleotide adaptor

The specific procedures were carried out as follows (see the procedures shown in FIG. 1):

The specific procedures:

1. mRNA Purification:

1) Standard, universal human reference RNA (3 μg, Agilent), was added into an RNase-free tube and diluted into 50 μl with DEPC. The obtained mixture was denatured at 65° C. for 5 min subsequent to evenly mixed to degrade the secondary structure of RNA, then immediately placed on ice to obtain a RNA sample.

2) 15 μl Dynalbeads Oligo (dT)$_{25}$ magnetic beads were added into a non-stick-EP tube, washed twice with 100 μl binding buffer, then re-suspended in 50 μl binding buffer, followed by added with the RNA sample obtained in 1), and last stood still for 5 min at room temperature.

3) The non-stick-EP tube was placed on MPC (magnetic separator) for 2 min to remove the supernatant. The remaining magnetic beads were washed twice with 200 μl washing buffer. 50 μl binding buffer was added to a new non-stick-EP tube.

4) The EP tube (i.e. non-stick-EP tube in 3)) containing magnetic beads was added with 50 μl 10 mM Tris-HCl and heated at 80° C. for 2 min to elute the mRNAs from the magnetic beads. Then the non-stick-EP tube was quickly transferred onto the MPC. The mRNAs were transferred into the new non-stick-EP tube containing the binding buffer in 3), the obtained mixture was denatured at 65° C. for 5 min to degrade the secondary structure of mRNAs, then immediately placed on ice. In addition, 200 μl washing buffer was immediately added into the tube containing the remaining magnetic beads to wash the magnetic beads twice.

5) 100 μl mRNA sample was added with magnetic beads washed twice and then stood still for 5 min at room temperature. The EP tube was placed on MPC for 2 min, the supernatant was carefully sucked out, and the remaining magnetic beads were washed twice with 200 μl washing buffer.

6) The EP tube containing magnetic beads was added with 17 μl 10 mM Tris-HCl, then heated at 80° C. for 2 min to elute mRNAs from the magnetic beads. The EP tube was quickly placed on MPC. The eluent containing mRNAs was transferred into a new 200 μl PCR tube. About 16 μl mRNAs was recycled.

2. Fragmentation of mRNA and Synthesis of a First Strand

After added with 3 μL 5× first strand buffer, the eluent obtained in previous step was firstly incubated at 94° C. for 10 min followed by immediately placed on ice, then added with 1 μl of random primers, and further incubated at 65° C. for 5 min to degrade the second structure followed by placed on ice. A reaction mixture, formulated with 100 mM DTT (2 μl), 25 mM dNTP mixture (0.4 μl) and RNase inhibitor (0.5 μl), was added into the tube containing RNA, followed by mixed to be uniform and then stood still for 2 min at room temperature, then added with 1 μl Superscript II (200 U/μl) and water up to 25 μl. PCR reaction was performed in accordance with the following procedures:

| Step 1 | 25° C. | 10 min |
| --- | --- | --- |
| Step 2 | 42° C. | 50 min |
| Step 3 | 70° C. | 15 min |
| Step 4 | 4° C. | hold |

3. Synthesis of a Second Strand

After the above PCR reaction, the resulting reaction system was added with water up to 82.8 μl, then mixed with 10 μl 5× second strand buffer and 1.2 μl 25 mM dNTP mixture in sequence to be uniform, followed by placed on ice for 5 min, and then mixed with 1 μl RNaseH and 5 μl DNA Pol I to be uniform. Such obtained reaction system for synthesizing a second strand was incubated at 16° C. for 2.5 h.

After the reaction was completed, the resulting double-stranded product was purified with Ampure XP magnetic beads, and the purified double-stranded product (DNAs) was dissolved in 50 μl EB buffer.

4. End-Repairing

50 μl solution containing double-stranded DNAs obtained in previous step was successively added with 27.4 μl water, 10 μl 10× end repair buffer, 1.6 μl 25 mM dNTP mixture, 5 μl T4 DNA polymases, 1 μl Klenow DNA polymases and 5 μl T4 PNK to form 100 μl reaction system which was incubated at 20° C. for 30 min.

After the reaction was completed, the end-repaired product was purified with Ampure XP magnetic beads and then dissolved in 32 μl EB buffer.

5. Base a Addition and Adaptor Ligation

32 μl solution containing end-repaired DNAs obtained in previous step was successively added with 5 μl A-tailing buffer, 10 μl 1 mM dATP and 3 μl Klenow exo (inhibiting activities of exonucleases for digesting from 3'-end to 5'-end) to form a reaction system of 50 μl, which was incubated at 37° C. for 30 min.

After the reaction was completed, the base A-added product was purified with Ampure XP magnetic beads and then dissolved in 23 μl EB buffer.

Figure 2:
FIG. 2 is a diagram showing the structure of a vesicular adaptor according to an embodiment of the present disclosure.

23 μl solution containing base A-added product obtained in previous step was successively added with 25 μl 2× Rapid T4 DNA Ligase Buffer, 1 μl vesicular adaptor (with a structure as shown in FIG. 2) mixture (containing the vesicular adaptor in an amount of 50 μmol) and 1 μl T4 DNA Ligase to form 50 μl reaction system, which was incubated at room temperature for 15 min.

The adaptor sequence was as follows:

(SEQ ID NO.: 1)
5'-GTCCTAAGACCNGATCGGGCTTCGACTGGAGACTCCGACTT-3'

(SEQ ID NO.: 2)
5'-/phos/AGTCGGAGGCCAAGCGGTCTTAGGACAT-3'.

After the reaction was completed, the ligation product was purified with Ampure XP magnetic beads, and then dissolved in 10 µl EB buffer.

6. PCR Amplification and Purification

30 µl solution containing adaptor-ligated product obtained in previous step was successively added with 10 µl 5× Phusion butter, 1 µl PCR Primer F (5-/phos/AGA-CAAGCTCNNNNNNNNNNNGATCGGGCTTCGACTG-GAGAC)(SEQ ID NO.:3), 1 µl PCR Primer R (5-/bio/TCCTAAGACCGCTTGGCCTCCGACT)(SEQ ID No.:4), 0.5 µl 25 mM dNTP mixture, 0.5 µl Phusion DNA polymases and 7 µl water to form 50 µl reaction system, which was incubated in the PRC instrument according to the following procedures:

a. 30 sec, 98° C.
b. 15 cycles:
10 sec, 98° C.
30 sec, 65° C.
30 sec, 72° C.
c. 5 min, 72° C.
d. hold 4° C.

Figure 3:
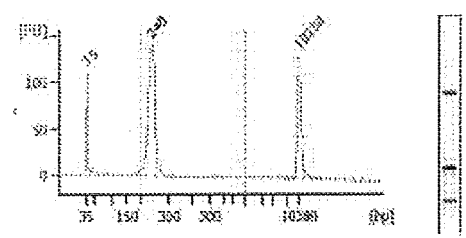
FIG. 3 is a diagram showing a result of a concentration of the purified PCR product detected by Agilent 2100 in nucleic acid library construction.

After the reaction was completed, the amplified PCR product was purified with Ampure XP magnetic beads and then dissolved in 32 µl EB buffer. The concentration of the purified PCR product was detected with Agilent 2100, and the results were shown in FIG. 3.

7. Isolation of a Single-Stranded Product 7.1 Washing magnetic beads coated with streptavidin 30 µl magnetic beads coated with streptavidin (for each sample) was mixed with 90 µl to 150 µl 1× magnetic beads binging buffer to be uniform in a non-stick tube, which was then placed on a magnetic separator for still standing and adsorption. The non-stick tube was adjusted to be in such a direction that enables the magnetic beads to move forward and backward in the 1× magnetic beads binging buffer, followed by discarding the supernatant. After direction adjustment step was repeated once, the non-stick tube was taken out from the magnetic separator, and added with 30 µl 1× magnetic beads binding buffer, followed by stood still at the room temperature.

7.2 After added with water up to 60 µl, the purified PCR product obtained in the step 6 was firstly mixed with 20 µl 4× magnetic beads binding buffer to be uniform, and then transferred into the non-stick tube obtained in 7.1 which contained magnetic beads dissolved in 30 µl 1× magnetic beads binding buffer, followed by mixing to be uniform. Such a resulting 110 µl mixture was incubated at room temperature for 15 to 20 min, during which the mixture was flicked gently once to make it distribute evenly.

7.3 The non-stick tube after the step 7.2 was placed on the magnetic separator for 3 to 5 min, followed by discarding the supernatant. The remaining magnetic beads were washed twice with 1 ml 1× magnetic beads washing buffer as described in step 7.1.

7.4 The magnetic beads after the step 7.3 were evenly mixed with 78 µl 0.1M NaOH by blowing up and down to obtain a mixture, followed by stood still for 10 min and then placed on the magnetic separator for 3 to 5 min. 74.5 µl supernatant thus obtained was transferred into a new 1.5 ml EP tube.

7.5 37.5 µl 0.3M MOPS was added into the 1.5 ml EP tube after the step 7.4, followed by mixed to be uniform, thereby obtaining 112 µl sample for use.

7.6 The 112 µl sample of can be stored at −20° C.

8. Cyclization of the Single-Stranded Product 8.1 A primer reaction solution was formulated as follows about 5 min in advance:

ON1587
(SEQ ID No.: 5)
(TCGAGCTTGTCTTCCTAAGACCGC)

| | |
|---|---|
| water | 43 µl |
| 20 µM ON1587 | 20 µl |
| Total volume | 63 µl |

8.2 63 µl primer reaction solution obtained in the step 8.1 was mixed by shaken thoroughly, centrifuged, and then added into the sample of 112 µl obtained in the step 7 (the starting amount n of the sample was critical and generally controlled within 100 ng≤n≤800 ng).

8.3 A ligase reaction solution was formulated as follows about 5 min in advance:

| | |
|---|---|
| water | 135.3 µl |
| 10× TA Buffer (LK1) | 35 µl |
| 100 mM ATP | 3.5 µl |
| 600 U/µl Ligase | 1.2 µl |
| total | 175 µl |

8.4 175 µl ligase reaction solution obtained in the step 8.3 was mixed by shaken thoroughly, centrifuged, and then added into the EP tube after the step 8.2 which contained the primer reaction solution, a mixture thus obtained in this step was mixed by shaken for 10 s to be uniform, and then centrifuged.

8.5 The mixture obtained in the step 8.4 was incubated in an incubator for 1.5 h at 37° C.

8.6 After the reaction was completed, 10 µl resulting sample was detected by electrophoresis detection with 6% denatured gel, and the remaining sample in about 350 µl was allowed to the next enzymatic reaction.

9. Enzyme Digestion 9.1 An enzyme-digesting reaction solution was formulated as follows about 5 min in advance:

| | |
|---|---|
| water | 1.5 µl |
| 10× TA Buffer (LK1) | 3.7 µl |
| 20 U/µl Exo I | 11.1 µl |
| 200 U/µl Exo III | 3.7 µl |
| total | 20 µl |

9.2 20 µl enzyme-digesting reaction solution obtained in the step 9.1 was mixed by shaken thoroughly, centrifuged, and then added into 350 µl sample obtained in the step 8.5 to obtain a mixture.

9.3 The mixture obtained in step 9.2 was mixed by shaken for 10 s to be uniform, and centrifuged, and then incubated in the incubator for 30 min at 37° C.

9.4 After 30 min, the enzymatic reaction was stopped by adding 15.4 µl 500 mM EDTA.

9.5 A sample obtained in the step 9.4 was purified with 1.3×PEG32 magnetic beads/Tween 20 (or Ampure XP magnetic beads) as follows:

The sample obtained in the step 9.4 was transferred into a 1.5 ml non-stick tube, and then added with 500 µl PEG32 magnetic beads, the mixture thus obtained was left for binding at room temperature for 15 min, during which the mixture was mixed once by blowing up and down to be uniform.

9.6 The non-stick tube after the step 9.5 was placed on the magnetic separator for 3 to 5 min, after which the supernatant was discarded, the remaining magnetic beads were washed twice with 700 µl 75% ethanol, during each of which the non-stick tube was reversed forward and backward to enable the magnetic beads to move 2 to 3 times in the ethanol.

9.7 The magnetic beads after washed were air dried, and then re-dissolved in 40 µl 1× TE for 15 min, during which the mixture thus obtained was mixed for one time to be uniform.

9.8 Supernatant from the mixture obtained in the step 9.8 was transferred into a new 1.5 ml EP tube, the final product was quantified with Qubit™ ssDNA Assay Kit.

Figure 4:
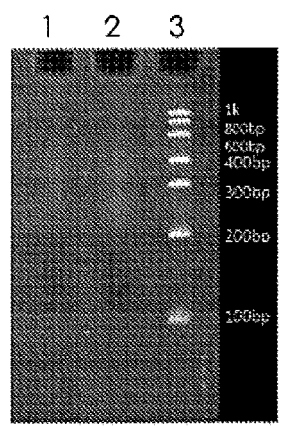
FIG. 4 is an electrophoretogram of libraries detected by the 6% of TBE denatured gel, where lanes 1 and 2 each represent a cyclic single-stranded library, while lane 3 represents low range ssRNA ladder.

9.9 5 µl sample and 2 µl low Range RNA ladder were respectively mixed with 5 µl 2×RNA loading buffer to be uniform in different PCR tubes, both of which was incubated at 95° C. for 2 min for denaturation in PCR instrument, and quickly cooled on ice for 5 min. The resulting samples were detected with 6% TBE denatured gel, the results is shown in FIG. 4.

9.10 Concentration standardization

Initial amount of the sample prepared with DNA nanoball (DNB) was uniformly adjusted to 7.5 fmol/µl in accordance with the concentration at which the single-stranded molecules were quantitatively detected.

Embodiment 2

Comparison of PCR efficiency of the vesicular adaptor in the library construction with that of other types of adaptors The specific steps were as follows:

Steps same as what described in Embodiment 1 were carried out, where one adaptor was the vesicular adaptor, and the comparison adaptor was matching adaptor. The PCR amplification and purification as described in the step 6 were completed, after which the amount of purified PCR product was detected.

Concentration of PCR template and recycling concentration were measured with Qubit dsDNA Assay Kit.

Experimental Result was Shown in Table

| Adaptor | Matching adaptor | Vesicular adaptor |
| --- | --- | --- |
| Amount of PCR template (ng) | 10 | 10 |
| Concentration of recycled product (ng/ul) | 5.66 | 53 |
| Total amount of recycled product (ng) | 226.4 | 2120 |
| PCR efficiency | 1.366 | 1.709 |

Note:
PCR efficiency = (total PCR yield/Initial amount of template) × (1/cycles)

It can be seen from above result that, PCR efficiency of the vesicular adaptor is apparently higher than that of the matching adaptor.

All documents mentioned in the present disclosure are incorporated herein by reference, as if each document were individually recited for reference. Furthermore, it should be appreciated that, those skilled in the art can make various changes and modifications to the present disclosure based on the content described above, and those equivalents also fall into the scope defined by appended claims of the present disclosure.

What is claimed is:

1. An oligonucleotide vesicular adaptor for constructing a nucleic acid library, comprising:
   a 5' paired double-stranded region at a first terminal of the adaptor;
   a 3' paired double-stranded region at a second terminal of the adaptor, comprising a first strand and a second strand complementary with each other, wherein the first strand of the 3' paired double-stranded region comprises an overhang at the 3' end thereof and the second strand of the 3' paired double-stranded region comprises a phosphorylated base at the 5' end thereof so as to provide a sticky terminal; and
   a vesicular non-paired region between the 5' paired double-stranded region and the 3' paired double-stranded region,
   wherein the vesicular non-paired region comprises a first strand and a second strand non-complementary with each other and the first strand of the vesicular non-paired region is of a length longer than that of the second strand of the vesicular non-paired region,
   wherein the vesicular adaptor is of a length between 20 nt to 50 nt.

2. The oligonucleotide vesicular adaptor according to claim 1, comprising a sense strand and an antisense strand and being of a structure of formula I from the 5' terminal to the 3' terminal:

$$Y0-Y1-Y2 \quad (I)$$

wherein
   Y0 represents the 5' paired double-stranded region, and is of a length of 10-15 nt;
   Y1 represents the vesicular non-paired region, the sense strand of the vesicular non-paired region being of a length 5-30 nt longer than that of the antisense strand;
   Y2 represents the 3' paired double-stranded region.

3. The oligonucleotide vesicular adaptor according to claim 2, wherein Y0 is of a length of 11 nt.

4. The oligonucleotide vesicular adaptor according to claim 1, wherein the sticky terminal of the 3' paired double-stranded region has a tailed single base.

5. The oligonucleotide vesicular adaptor according to claim 4, wherein the tailed single base is thymine (T).

6. The oligonucleotide vesicular adaptor according to claim 1, wherein the vesicular adaptor is of a length of 25 to 50 nt.

7. The oligonucleotide vesicular adaptor according to claim 1, wherein the vesicular adaptor is of a length of 30 to 45 nt.

8. The oligonucleotide vesicular adaptor according to claim 1, wherein the first strand of the vesicular non-paired region is longer than the second strand of the vesicular non-paired region by at least 5 to 30 nt.

9. The oligonucleotide vesicular adaptor according to claim 1, wherein the 5' paired double-stranded region also has a sticky terminal.

10. The oligonucleotide vesicular adaptor according to claim 1, wherein the 5' paired double-stranded region has a sticky terminal of 1 to 3 non-complementary bases.

11. A kit for constructing a nucleic acid library, comprising:
 a container;
 an oligonucleotide vesicular adaptor for constructing a library, wherein the oligonucleotide vesicular adaptor is contained in the container,
 wherein the oligonucleotide vesicular adaptor comprises:
  a 5' paired double-stranded region at a first terminal of the adaptor;
  a 3' paired double-stranded region at a second terminal of the adaptor, comprising a first strand and a second strand complementary with each other, wherein the first strand of the 3' paired double-stranded region comprises an overhang at the 3' end thereof and the second strand of the 3' paired double-stranded region comprises a phosphorylated base at the 5' end thereof so as to provide a sticky terminal; and
  a vesicular non-paired region between the 5' paired double-stranded region and the 3' paired double-stranded region,
 wherein the vesicular non-paired region comprises a first strand and a second strand non-complementary with each other and the first strand of the vesicular non-paired region is of a length longer than that of the second strand of the vesicular non-paired region,
 wherein the vesicular adaptor is of a length between 20 nt to 50 nt;
 a first primer, having the same sequence as at least a portion of the first strand of the vesicular non-paired region of the oligonucleotide vesicular adaptor;
 a second primer, specifically pairing with the second strand of the vesicular non-paired region of the oligonucleotide vesicular adaptor; and
 an instruction.

12. The kit according to claim 11, wherein the first primer is also provided as a sequencing primer.

13. A sequencing library for cyclic single-stranded nucleic acids constructed by the following steps of:
 (a) end-repairing a double-stranded DNA fragment to obtain a double-stranded DNA fragment with blunt terminals;
 (b) adding an adenine (A) base to each 3'-end of the double-stranded DNA fragment with the blunt terminals obtained in (a), to obtain a double-stranded DNA fragment with an A base at each 3'-end thereof;
 (c) ligating an oligonucleotide vesicular adaptor to each terminal of the double-stranded DNA fragment with the A base at each 3'-end thereof obtained in (b) to obtain a double-stranded DNA fragment ligated with the oligonucleotide vesicular adaptor at each terminal thereof, wherein the oligonucleotide vesicular adaptor comprises:
 a 5' paired double-stranded region at a first terminal of the adaptor;
 a 3' paired double-stranded region at a second terminal of the adaptor, comprising a first strand and a second strand complementary with each other, wherein the first strand of the 3' paired double-stranded region comprises an overhang at the 3' end thereof and the second strand of the 3' paired double-stranded region comprises a phosphorylated base at the 5' end thereof so as to provide a sticky terminal,
 wherein the sticky terminal of the 3' paired double-stranded region has a single base tail thymine (T); and
 a vesicular non-paired region between the 5' paired double-stranded region and the 3' paired double-stranded region,
 wherein the vesicular non-paired region comprises a first strand and a second strand non-complementary with each other and the first strand of the vesicular non-paired region is of a length longer than that of the second strand of the vesicular non-paired region,
 wherein the vesicular adaptor is of a length between 20 nt to 50 nt;
 (d) employing the double-stranded DNA fragment ligated with the oligonucleotide vesicular adaptor at each terminal thereof obtained in (c), as a template, for PCR amplification with a pair of primers so as to obtain a DNA amplified product, wherein one of the pair of primers is labeled with biotin
 wherein the pair of primers comprises
 a first primer having the same sequence as at least a portion of the first strand of the vesicular non-paired region of the oligonucleotide vesicular adaptor;
 a second primer, specifically pairing with the second strand of the vesicular non-paired region of the oligonucleotide vesicular adaptor;
 (e) isolating the single-stranded DNA labeled with biotin from the amplified double-stranded DNA product obtained in (d) by using beads coated with avidin through "avidin-biotin" combination, thus obtaining the single-stranded DNA minus biotin for cyclization;
 (f) subjecting the single-stranded DNA minus biotin obtained in (e) to cyclization in the presence of a cycling single-stranded molecule.

14. The sequencing library according to claim 5, wherein the double-stranded DNA fragment ligated with the oligonucleotide vesicular adaptor at each terminal thereof so as to provide a structure

K1-K2-K3 in which K1 and K3 each represent a vesicular adaptor ligated via the sticky terminal of said 3' paired double-stranded region, wherein K2 represents an arbitrary DNA sequence (sequence of a fragment to be sequenced); in which K1 and K3 are connected to K2 respectively at two terminals of K2.

15. The sequencing library according to claim 14, wherein K2 is of a length of 150 bp to 250 bp.

16. The sequencing library according to claim 13, wherein the sequencing library for cyclic single-stranded nucleic acids is constructed further by steps of:
 (g) digesting uncyclized DNAs obtained in (f) with nucleases specifically digesting linear DNAs to obtain a pre-product; and
 (h) purifying the pre-product obtained in (g) to obtain the cyclic single-stranded library.

17. The sequencing library according to claim 16, wherein the nucleases used in (g) comprise first exonucleases specifically digesting linear single-stranded DNAs and second exonucleases specifically digesting linear double-stranded DNAs.

* * * * *